United States Patent [19]

Kaneko

[11] Patent Number: 5,061,613
[45] Date of Patent: Oct. 29, 1991

[54] PYRAZOLO QUINAZOLONE COUPLER FOR PHOTOGRAPHY

[75] Inventor: Yutaka Kaneko, Tokyo, Japan

[73] Assignee: Konica Corporation, Tokyo, Japan

[21] Appl. No.: 450,060

[22] Filed: Dec. 13, 1989

[30] Foreign Application Priority Data

Dec. 20, 1988 [JP] Japan ............................. 63-321488

[51] Int. Cl.$^5$ ............................................. G03C 7/38
[52] U.S. Cl. .................................. 430/558; 430/384; 430/385
[58] Field of Search .................... 430/558 R, 384, 385

[56] References Cited

U.S. PATENT DOCUMENTS

| | | | |
|---|---|---|---|
| 3,171,740 | 3/1965 | Menzel et al. | 430/558 |
| 4,198,235 | 4/1980 | Vetter et al. | 430/223 |
| 4,473,632 | 9/1984 | Kitaguchi et al. | 430/223 |
| 4,873,183 | 10/1989 | Tachibana et al. | 430/558 |
| 4,950,585 | 8/1990 | Tachibana et al. | 430/558 |

OTHER PUBLICATIONS

J. Heterocyclic Chem. 6, pp. 947–948 (1969), Wright.

*Primary Examiner*—Richard L. Schilling
*Attorney, Agent, or Firm*—Frishauf, Holtz, Goodman & Woodward

[57] ABSTRACT

There is disclosed a coupler for photography of the formula (I):

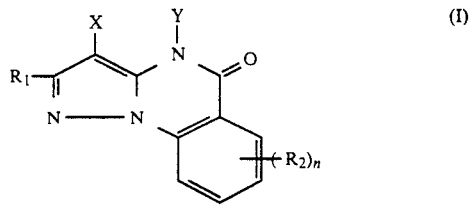

wherein $R_1$ and Y each represent a hydrogen atom or a substituent; $R_2$ represents a substituent; n represents an integer of 0 to 4, and when n is 2 or more, plural number of $R_2$'s may be the same or different; X represents a hydrogen atom or a substituent which is eliminated by the reaction with the oxidized product of a color developing agent.

10 Claims, No Drawings

PYRAZOLO QUINAZOLONE COUPLER FOR PHOTOGRAPHY

BACKGROUND OF THE INVENTION

This invention relates to a novel coupler for photography to be used as the material for color photography, particularly to a coupler for photography which forms a dye image excellent in fastness to heat, humidity and light.

After exposure is given to a light-sensitive silver halide photographic material, the material is subjected to color developing processing, whereby the oxidized aromatic primary amine color developing agent reacts with a dye forming coupler in the exposed region to form a dye, thereby forming a dye image.

Generally speaking, in such photographic method, the color reproduction method according to subtractive color system is used to form color images of yellow, magenta and cyan.

As the coupler for photography to be used for formation of yellow color image as mentioned above, there is, for example, an acylacetanilide type coupler. As the coupler for formation of magenta color image, there have been known, for example, pyrazolone, pyrazolobenzimidazole, pyrazolotriazole or indazolone type couplers. Further, as the coupler for formation of cyan color image, for example, phenol or naphthol type couplers are generally used.

The dye image thus obtained is desired to be not discolored or faded even when exposed to light, or stored under high temperature, high humidity for a long time.

However, the phenol type couplers and the naphthol type couplers which have been studied as the coupler for formation of cyan dye are not yet insufficient in such points as spectral absorption characteristics of the cyan dye image formed, heat resistance, humidity resistance and light resistance, etc., and various proposals have been made, including contrivances with respect to substituents, but no compound satisfying all of these has not yet been obtained.

Accordingly, the present inventors have progressed further study about the above-mentioned points, and consequently found a coupler for photography capable of forming a cyan dye image which does not cause color shift to heat, humidity and light, to accomplish the present invention.

SUMMARY OF THE INVENTION

A first object of the present invention is to provide a novel coupler for photography to be used as the material for color photography.

A second object of the present invention is to provide a coupler for photography for forming a cyan dye image which does not cause color shift to heat, humidity and light.

The above objects of the present invention have been accomplished by a coupler for photography represented by the formula (I):

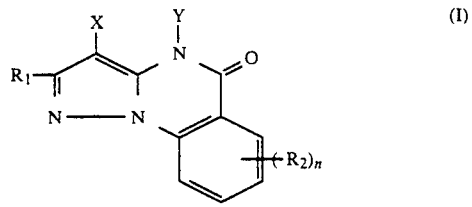

wherein $R_1$ and Y each represent a hydrogen atom or a substituent; $R_2$ represents a substituent; n represents an integer of 0 to 4, and when n is 2 or more, plural number of $R_2$'s may be the same or different; X represents a hydrogen atom or a substituent which is eliminated by the reaction with the oxidized product of a color developing agent.

DESCRIPTION OF THE PREFERRED EMBODIMENTS

The substituents represented by $R_1$ and $R_2$ in the formula (I) are not particularly limited, but representative examples may include respective groups of alkyl, aryl, anilino, acylamino, sulfonamide, alkylthio, arylthio, alkenyl, cycloalkyl, etc., and otherwise there may be also included halogen atoms and respective groups of cycloalkenyl, alkynyl, heterocyclic ring, sulfonyl, sulfinyl, phosphonyl, acyl, carbamoyl, sulfamoyl, cyano, alkoxy, sulfonyloxy, aryloxy, heterocyclicoxy, siloxy, acyloxy, carbamoyloxy, amino, alkylamino, imide, ureido, sulfamoylamino, alkoxycarbonylamino, aryloxycarbonylamino, alkoxycarbonyl, aryloxycarbonyl, heterocyclicthio, thioureido, carboxy, hydroxy, mercapto, nitro, sulfonic acid, etc., and also spiro compound residues, bridged hydrocarbon compound residues, etc.

Of the substituents represented by $R_1$ and $R_2$, those having 1 to 32 carbon atoms are preferred, which may be either straight or branched.

As the aryl group, phenyl group is preferred.

As the acylamino group, alkylcarbonylamino, arylcarbonylamino groups and the like may be included.

As the sulfonamide group, alkylsulfonylamino, arylsulfonylamino groups and the like may be included.

The alkyl component and the aryl component in the alkylthio and arylthio groups may include the alkyl and the aryl groups represented by $R_1$ and $R_2$ as mentioned above.

As the alkenyl group, those having 2 to 32 carbon atoms are preferred, as the cycloalkyl group, those having 3 to 12, particularly 5 to 7 carbon atoms are preferred, and the alkenyl group may be either straight or branched.

As the cycloalkenyl group, those having 3 to 12, particularly 5 to 7 carbon atoms are preferred.

The sulfonyl group may include alkylsulfonyl group, arylsulfonyl groups and the like; the sulfinyl group may include alkylsulfinyl, arylsulfinyl groups and the like; the phosphonyl group may include alkylphosphonyl, alkoxyphosphonyl, aryloxyphosphonyl, arylphosphonyl groups and the like; the acyl group may include alkylcarbonyl, arylcarbonyl groups and the like; the carbamoyl group may include alkylcarbamoyl, arylcarbamoyl groups and the like; the sulfamoyl group may include alkylsulfamoyl, arylsulfamoyl groups and the like; the acyloxy group may include alkylcarbonyloxy, arylcarbonyloxy groups and the like; the carbamoyloxy groups and the like; the ureido group may include alkylureido, arylureido groups and the like; the sulfamoylamino group may include alkylsulfamoylamino, arylsulfamoylamino groups and the like; the heterocyclic group may be preferably 5- to 7-membered one, specifically 2-furyl, 2-thienyl, 2-pyrimidinyl, 2-benzothiazolyl, 1-pyrrolyl, 1-tetrazolyl groups and the like; the heterocyclicoxy group may be preferably one having 5- to 7-membered heterocyclic ring, such as 3,4,5,6-tetrahydropyranyl-2-oxy, 1-phenyl-tetrazole-5-oxy groups and the like; the heterocyclicthio group may be preferably 5- to 7-membered heterocyclicthio group, such as 2-pyridylthio, 2-benzothiazolylthio, 2,4-diphenoxy-1,3,5-triazole-6-thio groups and the like; the siloxy group may include trimethylsiloxy, triethylsiloxy, dimethylbutylsiloxy groups and the like; the imide group may include succinicimide, 3-heptadecylsuccinicimide, phthalimide, glutarimide groups and the like; the spiro compound residue may include spiro[3,3-]heptan-1-yl and the like; the bridged hydrocarbon compound residue may include bicyclo[2,2,1]heptan1-yl, tricyclo[3,3,1,1$^{37}$]decan-1-yl, 7,7-dimethyl-bicyclo[2,2,1]heptan-1-yl and the like.

The above-mentioned groups may further have diffusionresistant substituents such as long chain hydrocarbon groups, polymer residues, etc.

n represents an integer of 0 to 4, and when n is 2 or more, plural number of $R_2$'s may be either the same or different. Also, two $R_2$'s may be bonded to further form a fused ring. As such fused ring, benzene ring may be included.

The substituents represented by $R_1$ preferably include respective groups of alkyl, aryl, anilino, acylamino, sulfonamide, alkylthio, arylthio, sulfonyl, acyl, carbamoyl, sulfamoyl, alkoxy and aryloxy.

The substituents represented by $R_2$ preferably include respective groups of alkyl, aryl, alkoxy, aryloxy, acylamino, sulfonamide, ureido and a halogen atom.

As the group eliminatable by the reaction with the oxidized product of a color developing agent represented by X, there may be included, for example, halogen atoms (chlorine, bromine, fluorine atoms, etc.), respective groups of alkoxy, aryloxy, heterocyclicoxy, acyloxy, sulfonyloxy, alkoxycarbonyloxy, aryloxycarbonyl, alkyloxalyloxy, alkoxyoxalyloxy, alkylthio, arylthio, heterocyclicthio, alkyloxythiocarbonylthio, acylamino, sulfonamide, nitrogen-containing heterocyclic ring bonded at N atom, alkyloxycarbonylamino, aryloxylcarbonylamino, carboxyl,

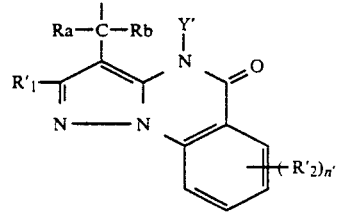

wherein $R_1'$ and $R_2'$ have the same meanings as $R_1$ and $R_2$ as described above, respectively; $Y'$ and $n'$ have the same meanings as Y and n as described above, respectively; and Ra and Rb each represent hydrogen atom, an aryl group, an alkyl group or a heterocyclic group, etc., preferably halogen atoms. Among them, particularly preferred ones represented by X are a hydrogen atom and a chlorine atom.

In the formula (I), Y represents a hydrogen atom or a substituent, and the preferred substituent represented by Y are, for example, those eliminated from the compounds of the present invention after the reaction of said compounds with the oxidized product of a developing agent. For example, the substituent represented by Y may include the groups eliminatable under alkaline conditions as disclosed in Japanese Provisional Patent Publication No. 228444/1986, substituents which are subjected to coupling off through the reaction with the oxidized product of a developing agent as disclosed in Japanese Provisional Patent Publication No. 133734/1981, etc., but preferably Y is a hydrogen atom.

Accordingly, the compounds represented by the formula (I) are more preferably represented by the formula (II):

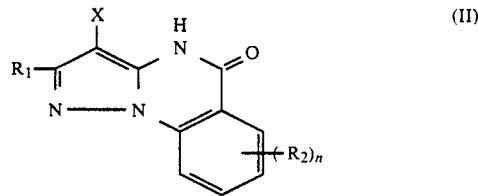

(II)

wherein $R_1$, $R_2$, n and X have the same meanings as $R_1$, $R_2$, n and X in the compounds represented by the formula (I), respectively.

In the following, representative exemplary compounds of the present invention are shown, by which the present invention is not limited at all.

| No. | R₁ | R₂ | n | X |
|---|---|---|---|---|
| 1 | —CH₃ | H | 0 | H |
| 2 | ⟨phenyl⟩ | H | 0 | H |
| 3 | —C₁₅H₃₁ | H | 0 | Cl |
| 4 | ⟨4-OC₁₂H₂₅-phenyl-NHSO₂-4-methylphenyl⟩ | H | 0 | H |
| 5 | —CH(CH₃)(CH₂)₂NHCO(CH₂)₃O—⟨3-C₁₅H₃₁-phenyl⟩ | H | 0 | Cl |
| 6 | —SCH₂—⟨4-(NHCOCH(C₆H₁₃)-O-2,4-di-t-C₅H₁₁-phenyl)-phenyl⟩ | H | 0 | Cl |
| 7 | ⟨3-NHSO₂C₁₁H₂₃-phenyl⟩ | H | 0 | H |

(II)

-continued (II)

| No. | R₁ | R₂ | n | X |
|---|---|---|---|---|
| 8 | —NH—⟨C₆H₄⟩—OC₁₈H₃₇ | H | 0 | Br |
| 9 | —OC₁₂H₂₅ | —OCH₃ (2) | 1 | Cl |
| 10 | —NHCONH—⟨C₆H₄⟩—C₁₁H₂₃ | —OCH₃ (2), —OCH₃ (3) | 2 | H |
| 11 | —CONHC₁₂H₂₅ | H | 0 | Cl |
| 12 | —SO₂N(C₈H₁₇)₂ | H | 0 | H |
| 13 | —COCH₂—⟨C₆H₄⟩—NHCOC₁₃H₂₇ | H | 0 | Cl |
| 14 | H | —NHCOC₁₁H₂₃ (2) | 1 | H |
| 15 | H | —OC₁₂H₂₅ (3) | 1 | H |
| 16 | —CH(CH₃)₂ | H | 0 | Cl |
| 17 | (methylenedioxyphenyl with C₄H₉(t), NHCOCHO, C₁₂H₂₅, p-tolyl substituents) | H | 0 | Cl |

-continued (II)

| No. | R₁ | R₂ | n | X |
|---|---|---|---|---|
| 18 | —SO₂CH₂—⟨C₆H₄⟩—OC₁₂H₂₅ | H | 0 | H |
| 19 | —C₁₂H₂₅ | H | 0 | H |
| 20 | —COOC₁₈H₃₇ | H | 0 | Cl |
| 21 | NHSO₂C₁₂H₂₅ (on o-tolyl) | Cl (1) | 1 | Cl |
| 22 | —SCH₃ | —NHSO₂C₁₂H₂₅ (4) | 1 | H |
| 23 | —⟨C₆H₄⟩—OC₁₂H₂₅ | —NHCOC₁₃H₂₇ (4) | 1 | H |
| 24 | —⟨C₆H₄Cl⟩—NHSO₂— | —OCH₃ (2), —OCH₃ (3) | 2 | H |
| 25 | —C(CH₃)₂—CH₂SO₂C₁₈H₃₇ | —NHCONHCH₃ (4) | 1 | Cl |
| 26 | —C₁₆H₃₃ | H | 0 | —⟨C₆H₄⟩—OCH₃ |

-continued $$(II)$$

Structure (II): A benzamide group (with $R_2$ substituents at positions 1-4 on phenyl ring) connected via -C(=O)-NH- to a pyrazole ring bearing $R_1$ and X substituents.

| No. | $R_1$ | $R_2$ | n | X |
|---|---|---|---|---|
| 27 | —NHC$_6$H$_5$ | Br (4) | 1 | H |
| 28 | 2-methylphenyl-NHCOC$_{11}$H$_{23}$ | —CH$_3$ (1)<br>—CH$_3$ (2)<br>—CH$_3$ (3)<br>—CH$_3$ (4) | 4 | H |
| 29 | 4-(OC$_{11}$H$_{23}$)phenyl-SO$_2$NH— | H | 0 | H |
| 30 | —CH$_3$ | Cl (3) | 1 | H |
| 31 | cyclohexyl (H) | —NHSO$_2$C$_{16}$H$_{33}$ (4) | 1 | Cl |
| 32 | —CH$_3$ | 2-(NHCOCHO-C$_8$H$_{17}$), 4-(C$_5$H$_{11}$(t))phenyl-NHCO— with C$_5$H$_{11}$(t) (4) | 1 | Cl |
| 33 | 4-(CH$_3$CH(CH$_2$)$_2$O)-C$_{15}$H$_{31}$-phenyl | —NHCOC$_4$H$_9$ (1) | 1 | H |

-continued (II)

| No. | $R_1$ | $R_2$ | n | X |
|---|---|---|---|---|
| 34 | $-C(CH_3)_3$ | $-NHSO_2$-(C_6H_4)-$OC_{12}H_{25}$ (1) | 1 | Cl |
| 35 | $-C_{16}H_{33}$ | 3-Cl, 4-NHCOCHO-$C_{10}H_{21}$ substituted phenylsulfonyl-(3-Cl,4-OH)phenyl (4) | 1 | H |
| 36 | $-SO_2CH_2C_6H_5$ | 4-$C_4H_9(t)$, 5-NHCOCHO-$C_{12}H_{25}$ substituted methylenedioxyphenyl (2) | 1 | H |
| 37 | $-NHCOCH_3$ | $-NHSO_2$-(C_6H_4)-$C_{18}H_{37}$ (4) | 1 | Cl |
| 38 | $-NH-C_6H_5$ | 2-Cl, NHCOCHO-$C_{12}H_{25}$ substituted phenyl (4) | 1 | $-S$-(C_6H_4)-$OCH_3$ |

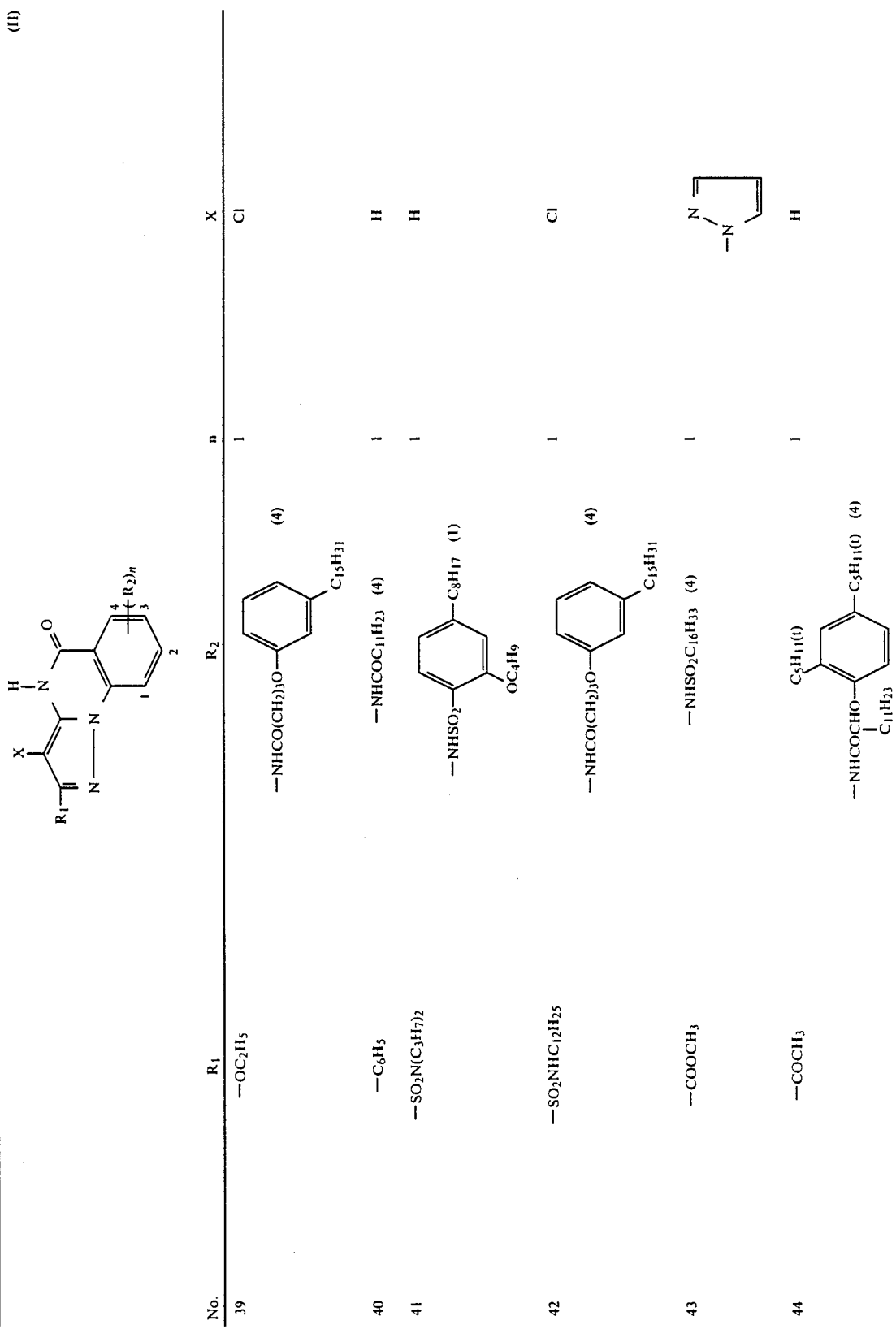

-continued (II)

[Structure: R1-substituted pyrazole with X and azo linkage to benzamide bearing (R2)n at positions 1,2,3,4]

| No. | R1 | R2 | n | X |
|---|---|---|---|---|
| 45 | —CH2—C6H4(NHCOC18H37) (meta) | —NHCOC2H5 (4) | 1 | Cl |
| 46 | —CH3 | 4-C8H17, 3-OC4H9, -NHSO2- phenyl | 1 | Cl |
| 47 | —C6H5 | benzodioxole with —NHCOC3H7(i) and OC4H9(t) (4) | 1 | H |
| 48 | —SO2N(CH3)2 | 3-C5H11(t), 5-C5H11(t), —NHCOC10H21 phenyl (3) | 1 | —N=N—C6H4(COOC2H5) (ortho) |
| 49 | —NHCOCH3 | 4-C8H17(t), 3-OC4H9, —NHSO2— phenyl (3) | 1 | [naphthalene substituted with NHCOCH3, OH, SO3K, KO3S, and —N=N—C6H4—OCH3 (para)] |

-continued $$\underset{R_1}{\overset{X}{\underset{N}{\parallel}}}\underset{N}{\overset{H}{\underset{N}{\parallel}}}\underset{1}{\overset{O}{\underset{2}{\bigcirc}}}\underset{3}{\overset{4}{(R_2)_n}}\quad (II)$$

| No. | $R_1$ | $R_2$ | n | X |
|---|---|---|---|---|
| 50 | $-C(CH_3)_3$ | $-NHSO_2-\bigcirc-OC_{12}H_{25}$ (3) | 1 | naphthol azo structure with OH, NHCOCH$_3$, SO$_3$K, KO$_3$S, N=N, and -O-CH$_3$ phenyl group |

Numerals in the branckets indicate the substitution positions.

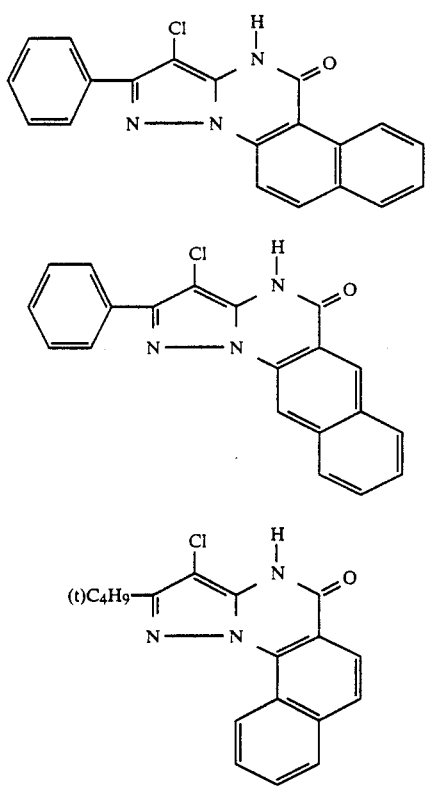

51.

52.

53.

Representative synthesis examples of the coupler of the present invention as described above are described below.

SYNTHESIS EXAMPLE 1 (SYNTHESIS OF EXEMPLARY COMPOUND 1)

In 160 ml of water was dissolved 38 g (0.2 mole) o-hydrazinobenzoic acid hydrochloride, and 40 ml of conc. hydrochloric acid was added to the resultant solution, and further 16.4 g (0.2 mole) of 3-aminocrotonnitrile was added to the mixture under stirring.

Boiling reflux of the above mixture was continued for 2.5 hours, followed by cooling, and the solid precipitated was recovered by filtration. After washing with water, recrystallization of the product from ethanol gave 25 g (0.12 mole) of white needle crystals. m.p. 286°–290° C. The structure was confirmed by NMR and mass spectrum.

SYNTHESIS EXAMPLE 2 (SYNTHESIS OF EXEMPLARY COMPOUND 30)

In 160 ml of water was dissolved 22.3 g (0.1 mole) of 5-chloro-2-hydrazinobenzoic acid hydrochloride, 40 ml of conc. hydrochloric acid was added to the resultant solution, and further 8.2 g (0.1 mole) of 3-aminocrotonnitrile was added to the mixture under stirring.

After the above mixture was stirred at room temperature for 30 minutes, boiling reflux was continued for 5 hours. After cooling, the solid precipitated was recovered by filtration, washed with water and recrystallized from ethanol to give 12 g (0.052 mole) of white needle crystals. m.p. 300°–305° C. The structure was confirmed by NMR and mass spectrum.

Other couplers of the present invention can be also synthesized according to the synthetic method as described above.

The coupler of the present invention can be used within the range generally from $1 \times 10^{-3}$ mole to 1 mole, preferably from $1 \times 10^{-2}$ mole to $8 \times 10^{-1}$ mole, per 1 mole of silver halide.

Also, the coupler of the present invention can be used in combination with other kinds of cyan couplers.

To the coupler of the present invention, the methods and the techniques used in conventional dye forming couplers are similarly applicable.

The coupler of the present invention can be used as the material for formation of color photography according to any color forming method, but specifically the external system color forming method and the internal system color forming method may be included. When used as the external system color forming method, the coupler of the present invention can be used by dissolving it in an aqueous alkali solution or an organic solvent (e.g. alcohol, etc.) and adding the solution into a developing processing solution.

When the coupler of the present invention is used as the material for formation of color photography according to the internal system color forming method, the coupler of the present invention is used by incorporating it in the photographic light-sensitive material. Typically, the method of formulating the coupler of the present invention in a silver halide emulsion and coating the emulsion on a support to form a color light-sensitive material may be preferably used. The coupler of the present invention may be used for a light-sensitive color photographic material such as color negative and positive films as well as color printing paper, etc.

The light-sensitive material using the coupler of the present invention, typically the color printing paper, may be either for monochromatic or multicolor use. In light-sensitive materials for use in multicolor, the coupler of the present invention may be contained in any layer, but ordinarily contained in red-sensitive silver halide emulsion layer. A light-sensitive material for multicolor has dye image forming constituent units having sensitivities to the respective three primary color regions. Each constituent unit can comprise a single layer or multilayer emulsion layer having sensitivity to a certain region of spectrum. The constituent layers of the light-sensitive material including the layer of image forming constituent can be arranged in various orders as known in this field of art. A typical light-sensitive material for multicolor comprises one having a cyan dye image forming constituent unit comprising at least one red-sensitive silver halide emulsion layer containing at least one cyan coupler (at least one of the cyan couplers is the cyan coupler of the present invention), a magenta dye image forming constituent unit comprising at least one green-sensitive silver halide emulsion layer containing at least one magenta coupler, and a yellow dye image forming constituent unit comprising at least one blue-sensitive silver halide emulsion containing at least one yellow coupler carried on a support.

The light-sensitive material can have additional layers such as filter layer, intermediate layer, protective layer, subbing layer, etc. For incorporating the coupler of the present invention in an emulsion, the method known of 175° C. or higher such as tricresyl phosphate, dibutyl phthalate, etc. or low boiling point solvents such as butyl acetate, butyl propionate, etc. alone or a mixture thereof, then mixing the resultant solution with an aqueous gelatin solution containing a surfactant, subsequently emulsifying the mixture by a high speed rotatory mixer or a colloid mill, followed by addition of a silver halide.

As the silver halide composition preferably used in the light-sensitive material in which the coupler of the present invention is used, there are silver chloride, silver chlorobromide or silver chloroiodobromide. Further, a combined mixture such as a mixture of silver chloride and silver bromide, etc. may be employed. More specifically, when the silver halide emulsion is used for a color printing paper, particularly rapid developability is demanded and therefore it is preferred to contain chlorine atoms as the halogen composition of the silver halide. Particularly, silver chloride, silver chlorobromide or silver chloroiodobromide each containing at least 1% of silver chloride is preferred.

The silver halide emulsion can be chemically sensitized in conventional manner. Also, it can be optically sensitized to a desired wavelength region.

In the silver halide emulsion, compounds known as antifoggant or stabilizer in the field of photography can be added for the purpose of preventing fog during the manufacturing steps, storage or photographic processing of the light-sensitive material, and/or maintaining stably the photographic performance.

In the color light-sensitive material using the coupler of the present invention, color antifoggants, dye image stabilizers, UV absorbers, antistatic agents, matte light-sensitive material, and/or maintaining stably the photographic performance.

In the color light-sensitive material using the coupler of the present invention, color antifoggants, dye image stabilizers, UV absorbers, antistatic agents, matte agents, surfactants, etc. conventionally used in light-sensitive materials can be used.

Concerning these agents, reference can be made to, for example, the description in Research Disclosure Vol. 176, pp. 22 to 31 (December, 1978).

The light-sensitive color photographic material using the coupler of the present invention can form an image by performing color developing processing known in this field of art.

The light-sensitive color photographic material using the coupler according to the present invention can contain a color developing agent as the color developing agent itself or as the precursor thereof in a hydrophilic colloid layer, and can be also processed with an alkaline activation bath.

The light-sensitive color photographic material using the coupler of the present invention is applied with bleaching processing, fixing processing after color developing. The bleaching processing may be also performed simultaneously with the fixing processing.

After the fixing processing, water washing processing is ordinarily performed. As alternative for water washing processing, stabilizing processing may be performed, or both may be also used in combination.

The present invention is described in detail below by referring to Examples, but the present invention is not limited to these Examples.

EXAMPLE 1

On a paper support laminated on both sides with polyethylene were coated successively the respective layers shown below from the support side to prepare a red-sensitive color light-sensitive sample 1. The amount of the compound added is shown per 1 m² unless otherwise particularly noted (silver halide is a value calculated on silver).

First layer: emulsion layer

A red-sensitive emulsion layer comprising 1.2 g of gelatin, 0.30 g of a red-sensitive silver chlorobromide emulsion (containing 96 mole % of silver chloride) and $9.1 \times 10^{-4}$ mole of a control cyan coupler a dissolved in 1.35 g of dioctyl phosphate.

Second layer: protective layer

Protective layer containing 0.50 g of gelatin. As the film hardener, 2,4-dichloro-6-hydroxy-s-triazine sodium salt was added to 0.017 g per 1 g of gelatin.

Next, samples 2 to 8 of the persent invention were prepared in entirely the same manner except that the control coupler a in the sample 1 was replaced with the couplers shown in Table 1 (amounts added are equimolar to the control coupler a).

The samples 1 to 8 obtained as described above were each given wedge exposure in conventional manner, and then subjected to developing processing in the next step.

| (Developing processing step) | | |
|---|---|---|
| Color developing | 38° C. | 3 min. 30 sec. |
| Bleach-fixing | 38° C. | 1 min. 30 sec. |
| Stabilizing/or water washing processing | 25° C.-30° C. | 3 min. |
| Drying | 75° C.-80° C. | 2 min. |

The processing solution compositions used in the respective processing steps are as shown below.
(Color developing solution)
  Benzyl alcohol: 15 ml
  Ethylene glycol: 15 ml
  Potassium sulfite: 2.0 g
  Potassium bromide: 0.7 g
  Sodium chloride: 0.2 g
  Potassium carbonate: 30.0 g
  Hydroxylamine sulfate: 3.0 g
  Polyphosphoric acid (TPPS): 2.5 g
  3-Methyl-4-amino-N-ethyl-N-($\beta$-methanesulfonamidoethyl)aniline sulfate: 5.5 g
  Fluorescent brightener: (4,4'-diaminostilbenesulfone derivative): 1.0 g
  Potassium hydroxide: 2.0 g
(made up to a total volume of one liter with addition of water, and adjusted to pH 10.20)
(Bleach-fixing solution)
  Ferric ammonium ethylenediaminetetraacetate dihydrate: 60 g
  Ethylenediaminetetraacetic acid: 3 g
  Ammonium thiosulfate (70% solution): 100 ml
  Ammonium sulfite (40% solution): 27.5 ml
(adjusted to pH 7.1 with potassium carbonate or glacial acetic acid, and made up to a total volume of one liter with addition of water)
(Stabilizing solution)
  5-Chloro-2-methyl-4-isothiazolin-3-one: 1.0 g
  Ethylene glycol: 10 g
(made up to one liter with addition of water)

For the samples 1 to 8 processed as described above, the densities were measured by use of a densitometer (KD-7R Model, manufactured by Konica Corp.), and further each sample was left to stand under high temperature and high humidity atmosphere (60° C., 80% RH) for 14 days, and heat and humidity resistance of the dye image was examined.

Also, after each sample was irradiated by a xenon fademeter for 10 days, the density was measured for examination of light resistance. The results are shown in Table 1. Heat resistance, humidity resistance and light resistance of the dye image are represented in residual dye percentage after heat and humidity resistance and light resistance tests based on the initial density 1.0.

Control coupler a

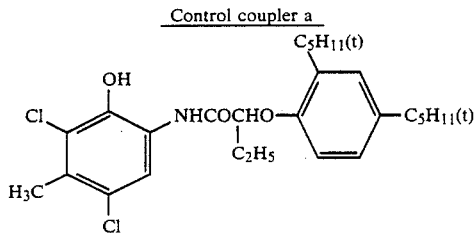

TABLE 1

| Sample No. | Coupler used | Residual dye percentage (%) Heat and humidity resistance | Light resistance |
| --- | --- | --- | --- |
| 1 | Control a | 64 | 84 |
| 2 | This invention 3 | 90 | 82 |
| 3 | This invention 7 | 88 | 83 |
| 4 | This invention 8 | 90 | 83 |
| 5 | This invention 20 | 89 | 84 |
| 6 | This invention 21 | 92 | 85 |
| 7 | This invention 22 | 91 | 84 |
| 8 | This invention 25 | 93 | 83 |

As is apparent from the results in Table 1, it can be understood that the samples by use of the couplers of the present invention are all higher in residual dye percentage, and faster with excellent heat and humidity resistance and light resistance as compared with the sample by use of the control coupler.

EXAMPLE 2

On a triacetate film subjected to the subbing treatment were successively coated the respective layers shown below from the support side to prepare a red-sensitive color light-sensitive material (sample 9). The amount of the compound added is shown per 1 m² unless otherwise particularly noted (silver halide is a value calculated on silver).

First layer:
Red-sensitive emulsion layer comprising 1.4 g of gelatin, 1.5 g of a red-sensitive silver iodobromide emulsion (containing 4 mole % of silver iodide) and $8.0 \times 10^{-4}$ mole of a control cyan coupler b dissolved in 1.1 g of tricresyl phosphate.

Second layer:
Protective layer containing 1.5 g of gelatin. As the film hardener, 2,4-dichloro-6-hydroxy-s-triazine sodium salt was added to 0.017 g per 1 g of gelatin.

Next, samples of the present invention 10 to 16 were prepared in entirely the same manner in Sample 9 except that the control cyan coupler b was replaced with the couplers shown in Table 2 (the amount added was the same mole amount as the control coupler b).

The film samples were wedge exposed in conventional manner and color developed following the processing steps for color shown below.

Control coupler b

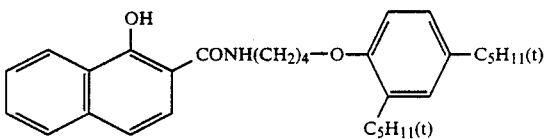

| [Processing step] | (Processing temperature 38° C.) | Processing time |
| --- | --- | --- |
| Color developing | | 3 min. 15 sec. |
| Bleaching | | 6 min. 30 sec. |
| Water washing | | 3 min. 15 sec. |
| Fixing | | 6 min. 30 sec. |
| Washing | | 3 min. 15 sec. |
| Stabilizing | | 1 min. 30 sec. |
| Drying | | |

The processing solution compositions used in the respective processing steps are as shown below.

(Color developing solution)
 4-Amino-3-methyl-N-ethyl-N-($\beta$-hydroxyethyl)aniline sulfate: 4.75 g
 Anhydrous sodium sulfite: 4.25 g
 Hydroxyamine ½ sulfate: 2.0 g
 Anhydrous potassium carbonate: 37.5 g
 Sodium bromide: 1.3 g
 Nitrilotriacetic acid trisodium (monohydrate): 2.5 g
 Potassium hydroxide: 1.0 g
(made up to one liter with addition of water, and adjusted to pH 10.6 by use of sodium hydroxide)

(Bleaching solution)
 Iron ammonium ethylenediaminetetraacetate: 100 g
 Diammonium ethylenediaminetetraacetate: 10.0 g
 Ammonium bromide: 150.0 g
 Glacial acetic acid: 10.0 g
(made up to a total volume of one liter with addition of water, and adjusted to pH 6.0 by use of aqueous ammonia)

(Fixing solution)
 Ammonium thiosulfate: 175.0 g
 Anhydrous sodium sulfite: 8.6 g
 Sodium matasulfite: 2.3 g
(made up to one liter with addition of water, and adjusted to pH 6.0 by use of acetic acid)

(Stabilizing solution)
 Formalin (37% aqueous solution): 1.5 ml
 Konidax (manufactured by Konica Corp.): 7.5 ml
(made up to one liter with addition of water)

For the samples 9 to 16 processed as described above, transmission densities were measured by use of a densitometer (KD-7R Model, manufactured by Konica K.K.), and further each processed sample was left to stand under high temperature and high humidity (60° C., 80% RH) for 14 days, and heat and humidity resistance of the dye image was examined.

Also, each sample was irradiated by a xenon fademeter for 10 days for examination of light resistance.

The results are shown in Table 2. Heat resistance, humidity resistance and light resistance of the dye image are represented in residual dye percentage after heat resistant, humidity resistant and light resistant tests based on the initial density 1.0.

TABLE 2

| Sample No. | Coupler used | Residual dye percentage (%) | |
|---|---|---|---|
| | | Heat and humidity resistance | Light resistance |
| 9 | Control b | 75 | 82 |
| 10 | This invention 9 | 85 | 80 |
| 11 | This invention 12 | 89 | 82 |
| 12 | This invention 19 | 90 | 81 |
| 13 | This invention 24 | 87 | 80 |
| 14 | This invention 31 | 91 | 84 |
| 15 | This invention 34 | 87 | 81 |
| 16 | This invention 40 | 90 | 85 |

As is apparent from the results in Table 2, it can be understood that the samples by use of the couplers of the present invention are all higher in residual dye percentage, and faster with excellent heat and humidity resistance and light resistance as compared with the sample by use of the control coupler.

EXAMPLE 3

On a triacetylcellulose film support, the respective layers were successively coated from the support side to prepare red-sensitive color reversal light-sensitive photographic materials 17 to 22 containing the couplers shown in Table 3.

First layer: emulsion layer

Red-sensitive emulsion layer comprising 1.4 g of gelatin, 0.5 g of a red-sensitive silver chlorobromide emulsion (containing 96 mole % of silver chloride) and $9.1 \times 10^{-4}$ mole of the coupler shown in Table 3 dissolved in 1.5 g of dibutyl phthalate.

Second layer: protective layer

Protective layer containing 0.5 g of gelatin. As the film hardener, 2,4-dichloro-6-hydroxy-s-triazine sodium salt was added to 0.017 g per 1 g of gelatin.

The samples obtained as described above were each given wedge exposure, and then subjected to developing processing in the next step.

| (Reversal processing steps) | | |
|---|---|---|
| Step | Time | Temperature |
| First developing | 6 min. | 38° C. |
| Washing | 2 min. | 38° C. |
| Reversal | 2 min. | 38° C. |
| Color developing | 6 min. | 38° C. |
| Adjusting | 2 min. | 38° C. |
| Bleaching | 6 min. | 38° C. |
| Fixing | 4 min. | 38° C. |
| Washing | 4 min. | 38° C. |
| Stabilizing | 1 min. | 38° C. |
| Drying | | normal temperature |

(First developing solution)
 Sodium tetrapolyphosphate: 2 g
 Sodium sulfite: 20 g
 Hydroquinone monosulfonate: 30 g
 Sodium carbonate (monohydrate): 30 g
 1-Phenyl-4-methyl-4-hydroxymethyl-3-pyrazolidone: 2 g
 Potassium bromide: 2.5 g
 Potassium thiocyanate: 1.2 g
 Potassium iodide (0.1% solution): 2 ml
 Water: to 1000 ml
(Reversal solution)
 Nitrilotrimethylenephosphonic acid hexasodium salt: 3 g
 Stannous chloride (dihydrate): 1 g
 p-Aminophenol: 0.1 g
 Sodium hydroxide: 5 g
 Glacial acetic acid: 15 ml
 Water: to 1000 ml
(Color developing solution)
 Sodium tetrapolyphosphate: 2 g
 Sodium sulfite: 7 g
 Sodium tertiary phosphate (12 hydrate): 36 g
 Potassium bromide: 1 g
 Potassium iodide (0.1% solution): 90 ml
 Sodium hydroxide: 3 g
 Citradinic acid: 1.5 g
 N-ethyl-N-($\beta$-methanesulfonamidoethyl)-3-methyl-4-aminoaniline sulfate: 11 g
 Ethylenediamine: 3 g
 Water: to 1000 ml
(Adjusting solution)
 Sodium sulfite: 12 g
 Sodium ethylenediaminetetraacetate (dihydrate): 8 g
 Thioglycerine: 0.4 ml
 Glacial acetic acid: 3 ml
 Water: to 1000 ml
(Bleaching solution)
 Sodium ethylenediaminetetraacetate (dihydrate): 2.0 g
 Iron (III) ammonium ethylenediaminetetraacetate (dihydrate): 120.0 g
 Potassium bromide: 100.0 g
 Water: to 1000 ml
(Fixing solution)
 Ammonium thiosulfate: 80.0 g
 Sodium sulfite: 5.0 g
 Sodium bisulfite: 5.0 g
 Water: to 1000 ml
(Stabilizing solution)
 Formalin (37% aqueous solution): 5.0 ml
 Konidax (manufactured by Konica Corp.): 5.0 ml
 Water: to 1000 ml The respective samples processed as described were examined for heat and humidity resistances and light resistance of the dye image similarly as in Example 2. The results are shown in Table 3.

TABLE 3

| Sample No. | Coupler used | Residual dye percentage (%) | |
|---|---|---|---|
| | | Heat and humidity resistance | Light resistance |
| 17 | Control a | 63 | 84 |
| 18 | This invention 32 | 91 | 84 |
| 19 | This invention 44 | 91 | 84 |
| 20 | This invention 45 | 89 | 85 |
| 21 | This invention 46 | 92 | 82 |
| 22 | This invention 47 | 93 | 84 |

As is apparent from Table 3, it can be understood that the samples by use of the couplers of the present invention are all higher in residual dye percentage, and faster with excellent heat and humidity resistances and light resistance as compared with the sample by use of the control coupler.

The dye image formed from the coupler of the present invention was found to be fast to heat, humidity and light.

I claim:

1. A light-sensitive silver halide photographic material having at least one photographic constituent layer, which comprises containing in said at least one photographic constituent layer, a coupler represented by a compound of the formula (I):

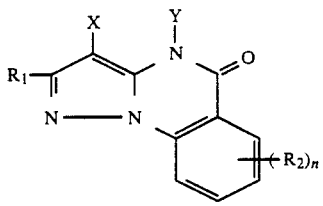

wherein $R_1$ and Y each represent a hydrogen atom or a substituent; $R_2$ represents a substituent; n represents an integer of 0 to 4, and when n is 2 or more, plural number of $R_2$'s may be the same or different; and X is a hydrogen atom or a halogen atom.

2. The photographic material according to claim 1, wherein said substituents for $R_1$ and $R_2$ are at least one selected from the group consisting of halogen atom, respective groups of alkyl, aryl, anilino, acylamino, sulfonamide, alkylthio, arylthio, alkenyl, cycloalkyl, cycloalkenyl, alkynyl, heterocyclic ring, sulfonyl, sulfinyl, phosphonyl, acyl, carbamoyl, sulfamoyl, cyano, alkoxy, sulfonyloxy, aryloxy, heterocyclicoxy, siloxy, acyloxy, carbamoyloxy, amino, alkylamino, imide, ureido, sulfamoylamino, alkoxycarbonylamino, aryloxycarbonylamino, alkoxycarbonyl, aryloxycarbonyl, heterocyclicthio, thioureido, carboxy, hydroxy, mercapto, nitro, sulfonic acid, spiro compound residues and bridged hydrocarbon compound residues.

3. The photographic material according to claim 2, wherein said substituents for $R_1$ and $R_2$ are at least one selected from the group consisting of halogen atom, respective groups of phenyl, alkylcarbonylamino, arylalkylsulfonyl, alkylsulfinyl, arylsulfinyl, alkylphosphonyl, alkoxyphosphonyl, aryloxyphosphonyl, arylphosphonyl, alkylcarbonyl, arylcarbonyl, alkylcarbamoyl, arylcarbamoyl, alkylsulfamoyl, arylsulfamoyl, alkylcarbonyloxy, arylcarbonyloxy, alkylcarbamoyloxy, arylcarbamoyloxy, alkylureido, arylureido, alkylsulfamoylamino, arylsulfamoylamino, 2-furyl, 2-thienyl, 2-pyrimidinyl, 2-benzothiazolyl, 1-pyrrolyl, 1-tetrazolyl, 3,4,5,6-tetrahydropyranyl-2-oxy, 1-phenyl-tetrazole-5-oxy, 2-pyridylthio, 2-benzothiazolylthio, 2,4-diphenoxy-1,3,5-triazole-6-thio, trimethylsiloxy, triethylsiloxy, dimethylbutylsiloxy, succinicimide, 3-heptadecylsuccinicimide, phthalimide, glutarimide, spiro[3,3]heptan-1-yl, bicyclo[2,2,1]heptan-1-yl, tricyclo[3,3,1,1$^{37}$]decan-1-yl and 7,7-dimethyl-bicyclo[2,2,1]heptan-1-yl.

4. The photographic material according to claim 2, wherein said $R_1$ is at least one selected from the group consisting of respective groups of alkyl, aryl, anilino, acylamino, sulfonamide, alkylthio, arylthio, sulfonyl, acyl, carbamoyl, sulfamoyl, alkoxy and aryloxy.

5. The photographic material according to claim 2, wherein said $R_2$ is at least one selected from the group consisting of halogen atom, respective groups of alkyl, aryl, alkoxy, aryloxy, sulfonamide and ureido.

6. The photographic material according to claim 1, wherein said X is a hydrogen atom or a chlorine atom.

7. The coupler of claim 1, wherein X is chlorine, bromine or fluorine.

8. A light-sensitive silver halide photographic material having at least one photographic constituent layer, which comprises containing in said at least one photographic constituent layer, a coupler represented by a compound of the formula (II) shown below with the substituents shown below:

| No. | R₁ | R₂ | n | X |
|---|---|---|---|---|
| 1 | —CH₃ | H | 0 | H |
| 2 | —C₆H₅ (phenyl) | H | 0 | H |
| 3 | —C₁₅H₃₁ | H | 0 | Cl |
| 4 | 4-(OC₁₂H₂₅)-C₆H₄-NHSO₂-C₆H₄- | H | 0 | H |
| 5 | —CH(CH₃)CH(CH₂)₂NHCO(CH₂)O-C₆H₄-C₁₅H₃₁ | H | 0 | Cl |
| 6 | 4-[C₅H₁₁(t)]-2-[C₅H₁₁(t)]-C₆H₃-O-CH(C₆H₁₃)-CONH-C₆H₄-SCH₂— | H | 0 | Cl |
| 7 | 3-(NHSO₂C₁₁H₂₃)-C₆H₄— | H | 0 | H |

(II)

-continued (II)

| No. | R₁ | R₂ | n | X |
|-----|-----|-----|---|---|
| 8 | −NH−⟨C₆H₄⟩−OC₁₈H₃₇ | H | 0 | Br |
| 9 | −OC₁₂H₂₅ | −OCH₃ (2) | 1 | Cl |
| 10 | −NHCONH−⟨C₆H₄⟩−C₁₁H₂₃ | −OCH₃ (3) | 2 | H |
| 11 | −CONHC₁₂H₂₅ | H | 0 | Cl |
| 12 | −SO₂N(C₈H₁₇)₂ | H | 0 | H |
| 13 | −COCH₂−⟨C₆H₄⟩−NHCOC₁₃H₂₇ | H | 0 | Cl |
| 14 | H | −NHCOC₁₁H₂₃ (2) | 1 | H |
| 15 | H | −OC₁₂H₂₅ (3) | 1 | H |
| 16 | −CH(CH₃)₂ | H | 0 | Cl |
| 17 | −NHCOCHO−⟨aryl⟩ (C₄H₉(t), O−CH₂−O, C₁₂H₂₅, p-tolyl) | H | 0 | Cl |

| No. | R$_1$ | R$_2$ | n | X |
|-----|-----|-----|---|---|
| 8 | −NH−C₆H₄−OC$_{18}$H$_{37}$ | H | 0 | Br |
| 9 | −OC$_{12}$H$_{25}$ | −OCH$_3$ (2) | 1 | Cl |
| 10 | −NHCONH−C₆H₄−C$_{11}$H$_{23}$ | −OCH$_3$ (3) | 2 | H |
| 11 | −CONHC$_{12}$H$_{25}$ | H | 0 | Cl |
| 12 | −SO$_2$N(C$_8$H$_{17}$)$_2$ | H | 0 | H |
| 13 | −COCH$_2$−C₆H₄−NHCOC$_{13}$H$_{27}$ | H | 0 | Cl |
| 14 | H | −NHCOC$_{11}$H$_{23}$ (2) | 1 | H |
| 15 | H | −OC$_{12}$H$_{25}$ (3) | 1 | H |
| 16 | −CH(CH$_3$)$_2$ | H | 0 | Cl |
| 17 | −NHCOCHO−aryl(C$_4$H$_9$(t), methylenedioxy, C$_{12}$H$_{25}$, p-tolyl) | H | 0 | Cl |

-continued
$$\text{(II)}$$
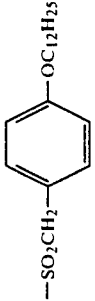
| No. | R₁ | R₂ | n | X |
|---|---|---|---|---|
| 18 | —SO₂CH₂—〈C₆H₄〉—OC₁₂H₂₅ | H | 0 | H |
| 19 | —C₁₂H₂₅ | H | 0 | H |
| 20 | —COOC₁₈H₃₇ | H | 0 | Cl |
| 21 | —NHSO₂C₁₂H₂₅〈o-tolyl〉 | Cl (1) | 1 | Cl |
| 22 | —SCH₃ | —NHSO₂C₁₂H₂₅ (4) | 1 | H |
| 23 | —〈C₆H₄(CH₃)〉—OC₁₂H₂₅ | —NHCOC₁₃H₂₇ (4) | 1 | H |
| 24 | —〈C₆H₄(Cl)〉—NHSO₂ | —OCH₃ (2), —OCH₃ (3) | 2 | H |
| 25 | —C(CH₃)₂CH₂SO₂C₁₈H₃₇ | —NHCONHCH₃ (4) | 1 | Cl |

-continued (II)

| No. | R₁ | R₂ | n | X |
|---|---|---|---|---|
| 26 | —C₁₆H₃₃ | H | 0 | 4-methoxyphenyl (—C₆H₄—OCH₃) |
| 27 | —NHC₆H₅ | Br (4) | 1 | H |
| 28 | 2-methyl-NHCOC₁₁H₂₃-phenyl | —CH₃ (1)<br>—CH₃ (2)<br>—CH₃ (3)<br>—CH₃ (4) | 4 | H |
| 29 | 4-OC₁₁H₂₃-phenyl-SO₂NH— | H | 0 | H |
| 30 | —CH₃ | Cl (3) | 1 | Cl |
| 31 | cyclohexyl (H) | —NHSO₂C₁₆H₃₃ (4) | 1 | Cl |
| 32 | —CH₃ | 2-C₅H₁₁(t), 4-C₅H₁₁(t), —NHCOCHO—C₈H₁₇ phenyl | 1 | Cl |

-continued (II)

[Structure: benzamide with (R2)n on positions 1-4 of phenyl ring, NH connected to C=N-N=C-R1 with X substituent]

| No. | R1 | R2 | n | X |
|---|---|---|---|---|
| 33 | —CH(CH2)2O—C6H4—C15H31 (with CH3 branch) | —NHCOC4H9 (1) | 1 | H |
| 34 | —C(CH3)3 | —NHSO2—C6H4—OC12H25 (1) | 1 | Cl |
| 35 | —C16H33 | —NHCOCHC10H21—C6H3(Cl)—SO2—C6H3(Cl)—OH (4) | 1 | H |
| 36 | —SO2CH2C6H5 | —NHCOCHC12H25—[benzodioxole, C4H9(1)] (2) | 1 | H |
| 37 | —NHCOCH3 | —NHSO2—C6H4—C18H37 (4) | 1 | Cl |
| 38 | —NH—C6H5 | —NHCOCHC12H25—C6H3(Cl) (4) | 1 | —S—C6H4—OCH3 |

-continued (II)

[Structure: benzamide with hydrazone substituent, positions 1-4 on ring with (R₂)ₙ]

| No. | R₁ | R₂ | n | X |
|---|---|---|---|---|
| 39 | —OC₂H₅ | —NHCO(CH₂)₃O—C₆H₄—C₁₅H₃₁ (4) | 1 | Cl |
| 40 | —C₆H₅ | —NHCOC₁₁H₂₃ (4) | 1 | H |
| 41 | —SO₂N(C₃H₇)₂ | —NHSO₂—C₆H₃(C₈H₁₇)(OC₄H₉) (1) | 1 | H |
| 42 | —SO₂NHC₁₂H₂₅ | —NHCO(CH₂)₃O—C₆H₄—C₁₅H₃₁ (4) | 1 | Cl |
| 43 | —COOCH₃ | —NHSO₂C₁₆H₃₃ (4) | 1 | pyrazolyl |
| 44 | —COCH₃ | —NHCOCH(C₁₁H₂₃)—C₆H₃(C₅H₁₁)(C₅H₁₁) | 1 | H |

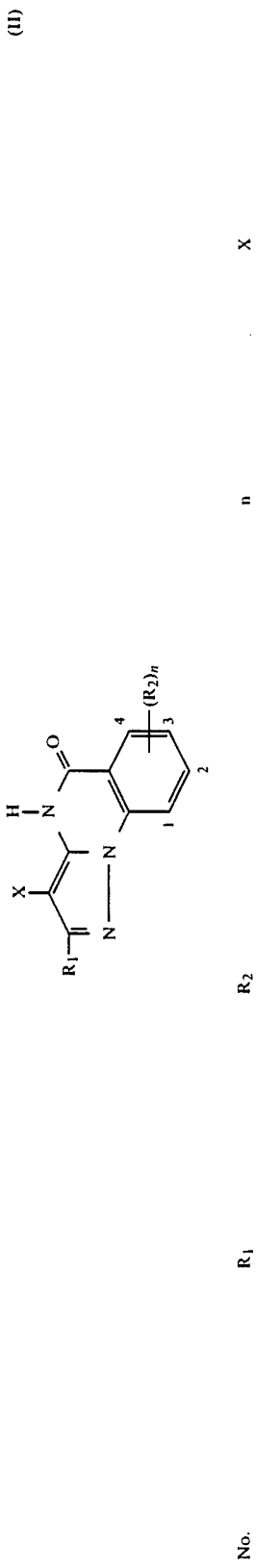

-continued (II) [structure: benzamide with NH-C(=O), X, R₁, and (R₂)ₙ on phenyl with positions 1,2,3,4]

| No. | R₁ | R₂ | n | X |
|---|---|---|---|---|
| 50 | —C(CH₃)₃ | —NHSO₂—⟨C₆H₄⟩—OC₁₂H₂₅ (3) | 1 | —O—⟨C₆H₄⟩—N=N—⟨naphthalene with OH, NHCOCH₃, SO₃K, SO₃K⟩ | numerals in the brackets indicate the substitution positions.

9. The photographic material according to claim 8, wherein said coupler is used within the range from $1 \times 10^{-3}$ mole to 1 mole per 1 mole of silver halide in the constituent layer.

10. The photographic material according to claim 9, wherein said coupler is used within the range of from $1 \times 10^{-2}$ mole to $8 \times 10^{-1}$ mole per 1 mole of silver halide in the constituent layer.

* * * * *